United States Patent [19]

Onaga et al.

[11] Patent Number: 4,816,800
[45] Date of Patent: Mar. 28, 1989

[54] EXHAUST GAS SENSOR

[75] Inventors: Kazuo Onaga, Toyonaka; Katsuyuki Tanaka, Suita; Kazunari Komatsu, Hiroshima, all of Japan

[73] Assignees: Figaro Engineering Inc., Osaka; Mazda Motor Corp., Hiroshima, both of Japan

[21] Appl. No.: 883,130

[22] Filed: Jul. 8, 1986

[30] Foreign Application Priority Data

Jul. 11, 1985 [JP] Japan ................................ 60-152914
Jul. 11, 1985 [JP] Japan ................................ 60-152915

[51] Int. Cl.$^4$ ............................................. H01L 7/00
[52] U.S. Cl. ........................................ 338/34; 338/35; 73/27 R
[58] Field of Search ................... 338/34, 35; 73/27 A, 73/23, 27 R

[56] References Cited

U.S. PATENT DOCUMENTS

| | | | |
|---|---|---|---|
| 4,314,996 | 2/1982 | Sekido et al. | 338/34 X |
| 4,485,369 | 11/1984 | Ushida | 338/34 |
| 4,490,715 | 12/1984 | Kusanagi et al. | 338/34 X |
| 4,507,643 | 3/1985 | Sunano et al. | 338/34 |

*Primary Examiner*—E. A. Goldberg
*Assistant Examiner*—Marvin M. Lateef
*Attorney, Agent, or Firm*—Kane, Dalsimer, Sullivan, Kurucz, Levy, Eisele and Richard.

[57] ABSTRACT

An exhaust gas sensor in which a metal oxide semiconductor containing at least one member of a group of elements consisting of Sn, Fe, Ni and Co and Pt electrodes having $ZrO_2$, deposited in the grain boundary are used.

9 Claims, 6 Drawing Sheets

EXHAUST GAS SENSOR

BACKGROUND OF THE INVENTION

1. Field of the Invention

The present invention relates to an improvement in exhaust gas sensors utilizing a change in resistance value of metal oxide semiconductors, and more particularly to an improvement in durability of electrodes. The exhaust gas sensor of the invention is suitable for detection of the air-fuel ratio in automobile engines, space heaters or boilers, etc.

2. Prior Art

Hitherto, a problem that Pt electrodes of an exhaust gas sensor are corroded by high temperature reducing atmosphere has been well known. For example, U.S. Pat. No. 4,237,722 proposes the use of a Pt-Rh alloy as highly durable electrodes, disclosing that such corrosion is caused by reaction of Pt with carbon in the exhaust gases.

The inventors' tests confirmed that the Pt-Rh alloy had excellent durability, when $TiO_2$ was used as a metal oxide semiconductor (Table 2), but the situation is quite different with compounds containing an Sn compound such as $SnO_2$, $BaSnO_3$, etc. When the Pt-Rh alloy electrodes are used with these compounds, the electrodes are corroded in high temperature reducing atmospheres. The Pt-Rh alloy electrodes are effective with $TiO_2$, but are ineffective with $BaSnO_3$ or $SnO_2$, etc. Elementary analysis of corroded electrodes revealed the formation of solid solutions of Pt and Sn. The cause of corrosion is not the reaction of Pt with carbon, but the formation of an alloy of Pt and Sn.

The inventors further found that Pt-Rh electrodes were corroded by metal oxide semiconductors, including Fe, Ni, or Co elements, because of the alloy formation with Pt. When these elements are used, the electrodes are corroded in a high temperature reducing atmosphere. Main materials of exhaust gas sensors containing these elements include such perovskite compounds as $SrFeO_3$, $LaNiO_3$ and $LaCoO_3$, etc.

According to related prior arts, $TiO_2$ is a representative exhaust gas sensor material and its characteristics are described in U.S. Pat. No. 3,886,785, etc. $SrFeO_3$, $LaNiO_3$ and $LaCoO_3$ are p-type metal oxide semiconductors and their resistance values diminish with oxygen concentrations and increase with combustible gas concentrations. These compounds all have crystalline structure of perovskite type, and characteristics of $SrFeO_3$ are described, for example, in U.S. Pat. No. 3,558,280, while those of $LaCoO_3$ and $LaNiO_3$, for example, in "Proceedings of the International Meeting on Chemical Sensors" (Kodansha 1983) and U.S. Pat. No. 4,507,643, etc. $SnO_2$ is an n-type metal oxide semiconductor, and its characteristics are well-known as shown in U.S. Pat. No. 4,459,577, etc. Metal oxide semiconductors such as $BaSnO_3$, $CaSnO_3$ and $SrSnO_3$, etc., are perovskite compounds and novel materials for exhaust gas sensors. Characteristics of these compounds are described in U.S. patent application No. 807,257 (Dec. 10, 1985) filed by the same assignee, and its descriptions will be cited hereinafter.

SUMMARY OF THE INVENTION

The object of the present invention is to prevent electrodes from corrosion due to the formation of an alloy of Pt and the metal element in a metal oxide semiconductor.

The exhaust gas sensor of this invention is characterized by combining a metal oxide semiconductor containing either one of elements,—Sn, Fe, Ni or Co—with Pt electrodes having $ZrO_2$ deposited in the crystalline grain boundaries.

Such metal oxide semiconductors include, for example, $SnO_2$, $BaSnO_3$, $SrSnO_3$, $CaSnO_3$. And other metal oxide semiconductors include $SrFeO_3$, $LaNiO_3$, $LaCoO_3$, $La_{1-x}Sr_xNi_{1-y}Co_yO_3$, etc. These metal oxide semiconductors need not be used alone, but they can be used in mixtures with other metal oxide semiconductors, e.g., $TiO_2$, etc., or with a part of component elements substituted by other metal elements, or further, in mixtures of $SnO_2$, etc. with $BaSnO_3$, etc. It is, of course, permissible to add some known additives such as noble metal catalyzers, etc. to such semiconductors.

It is only necessary that the electrodes are mainly composed of Pt and $ZrO_2$ and are deposited in the crystal boundaries thereof. Those with such third components as Rh, Au, etc., added are also preferable.

The preferable amount of $ZrO_2$ is $0.01 \sim 3.0$ in weight % concentration and more preferably $0.1 \sim 2.0$.

PREFERRED EMBODIMENTS

Manufacture of Exhaust Gas Sensors (1) $BaCO_3$, $SrCO_3$ or $CaCO_3$ was mixed with $SnO_2$ in equimolar ratio to react them in air at 1200° C. for 4 hr, yielding a perovskite compound of $BaSnO_3$, $SrSnO_3$ or $CaSnO_3$. The compound thus obtained was pulverized and Pt electrodes with $ZrO_2$ (70 μin diameter, Tanaka Noble Metal Industry, Ltd.) available on the market were embedded therein, then was molded into a sensor chip shown in FIGS. 1 and 2. The chip thus molded was baked by heating in air at 1300° C. for 4 hours. The Pt electrode with $ZrO_2$ deposited in the crystal grain boundaries is hereinafter referred to as Pt-$ZrO_2$ electrode.

Figure 1:
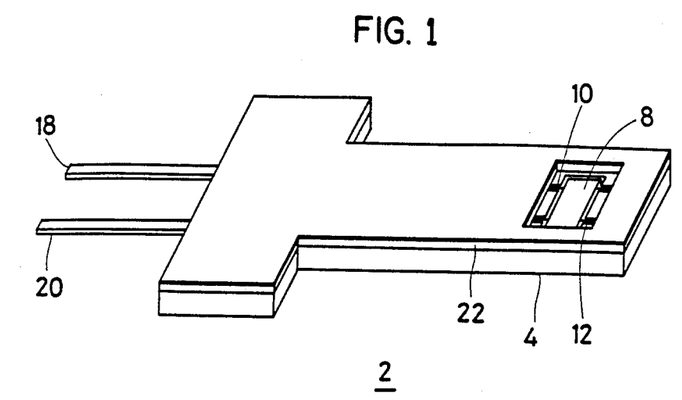
FIG. 1 is a perspective view of an exhaust gas sensor of the embodiment.
Figure 2:
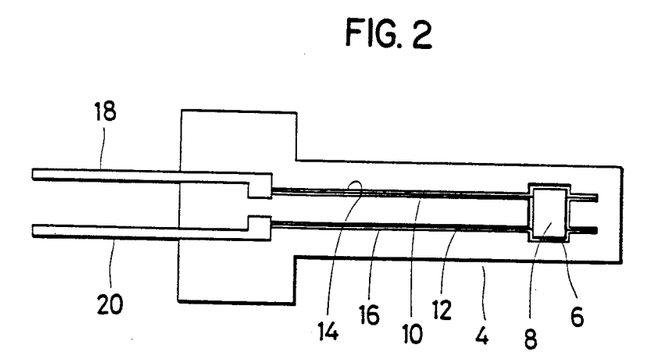
FIG. 2 is a plan view showing an exploded state of the exhaust gas sensor of the embodiment.

With the chip which has been sintered, an exhaust gas sensor (2) shown in FIGS. 1 and 2 was assembled. In these drawings, (4) denotes an insulating substrate of alumina, etc.; in the recess (6) provided at one end thereof, the sensor chip (8) is housed. Electrodes (10) and (12) on the chip (8) are housed in grooves (14) and (16) provided in the substrate (4), with their ends connected to base metal outside leads (18) and (20). Then an alumina sheet (22) is pasted on the substrate (4), leaving a gap along the circumferential rim of the chip (8), thereby shielding and protecting the electrodes (10) and (12) from the atmosphere. Any constructions of gas sensor (2) other than this can be employed as a matter of course.

(2) Similarly, Pt-ZrO$_2$ electrodes are connected with SnO$_2$ which has been calcined at 1200° C. and, then, this product is sintered at 1300° C., yielding a similar gas sensor (2).

(3) SrCO$_3$ and Fe$_2$O$_3$ are mixed in equi-molar ratio. The mixture is, then, calcined in air at 1200° C. for 4 hr, yielding a perovskite compound SrFeO$_3$. This product is connected with Pt-ZrO$_2$ electrodes, similarly as in the case of (1), and is sintered at 1300° C., forming a sensor (2). Similarly, by reaction of lanthanum oxalate with NiO and that of lanthanum oxalate with CoO, a sensor (2) in which LaNiO$_3$ and LaCoO$_3$ are used are obtained. These manufacturing methods (1)~(3) are equivalent, except for the semiconductors used.

(4) As comparative examples, the following sensors (2) are prepared:

(a) A sensor in which the Pt-ZrO$_2$ electrodes (10) and (12) are substituted by 80$\mu$ dia. Pt-Rh alloy electrodes (Rh 40% or 13% by weight).

(b) A sensor in which Pt (80$\mu$ dia.) with 1.0% by weight of TiO$_2$ deposited is used as the electrodes.

(c) A sensor in which Pt electrodes (70$\mu$ dia.) with 5% by weight of Au added are used.

(d) A sensor in which Pt-Rh alloy (Rh 40% by weight) is used as electrodes for TiO$_2$.

In these comparative examples, the manufacturing conditions of the sensor (2) are equivalent except for electrodes.

Characteristics of Semiconductors

SnO$_2$ is well-known as a material of exhaust gas sensors. On the other hand, BaSnO$_3$, SrSnO$_3$ and CaSnO$_3$ are novel as exhaust gas sensor materials; they are all perovskite compounds. BaSnO$_3$ is an n-type metal oxide semiconductor; its resistance value increases with air-fuel ratios in full range. SrSnO$_3$ and CaSnO$_3$ are compounds which have both the n- and p-type properties blended; thus, in a region (lean region) where the equivalent ratio $\lambda$ is larger than 1, the resistance value diminishes with air-fuel ratios, thus showing the p-type property; while at the equivalent point ($\lambda=1$) or in rich region (a region in which $\lambda$ is smaller than 1), the n-type property is apparent, with the resistance value increasing with air-fuel ratios.

Among these compounds, BaSnO$_3$ is most excellent. The oxygen sensitivity of BaSnO$_3$ is higher than those of SrSnO$_3$ or CaSnO$_3$. Oxygen sensitivities of BaSnO$_3$ and SnO$_2$ are on the same order, but BaSnO$_3$ is superior in its durability in reducing atmospheres and in the smaller detection errors due to unreacted inflammable gases in the exhaust gases. For example, when SnO$_2$ is exposed for a long time (4~10 hr) to atmospheres with the equivalent ratios 0.9~0.95 at 900° C., its resistance value irreversibly falls, but such a phenomenon does not occur with BaSnO$_3$. Then, SnO$_2$ shows high sensitivity to unreacted components (mainly CO and HC) in exhaust gases, but BaSnO$_3$ gives a low value. Because of the SnO$_2$'s sensitivity to unreacted components being too high, as compared with that to oxygen, variations in the amounts of the unreacted components result in detection errors.

In the following, comparison results between BaSnO$_3$ and SnO$_2$ are cited from the description of U.S. patent application No. 807,257 (Table 1).

To the sample, 5 mol-% of SiO$_2$ (silica colloid) is added. Silica hardly exerts influence on durability in reducing atmospheres or the sensitivities to such inflammable gases as carbon monoxide, etc. The addition of silica increases the oxygen gradient of BaSnO$_3$ from 0.18 to 0.22. However, silica hardly affects the oxygen gradient of SnO$_2$.

It is evident that BaSnO$_3$ is superior to SnO$_2$ in the aspect of durability against the high temperature reducing atmosphere. Further, BaSnO$_3$ gives small detection error, when unreacted inflammable gases are remaining in the lean region. In Table 1, on the assumption of chemical equilibrium between carbon monoxide, and oxygen, the ratio of its resistance in 1,000 ppm CO to that in 10,000 ppm CO is 1.02, as calculated from the oxygen gradient. With BaSnO$_3$, by addition of a small amount of some noble metal catalyzer or by providing an oxidizing catalyzer layer outside the sensor, the error due to coexistence of inflammable gases may be eliminated. In contrast, with SnO$_2$, the detection error is large, CaSnO$_3$ or SrSnO$_3$ is superior to SnO$_2$ in the aspects of durability and small detection error due to inflammable gases.

TABLE 1

| | BaSnO$_{3-\delta}$ vs. SnO$_2$ | | |
| Specimen | Reduction of resistance due to endurance test*[1] (Rso/Rsf) | CO sensitivity*[2] (R$_s$co1000/R$_s$co10,000) | Oxygen gradient*[3] (at 700° C.) |
| --- | --- | --- | --- |
| BaSnO$_{3-\delta}$ + SiO$_2$ 5 mol % 1400° C. baking | 1.0 | 1.9 | 0.22 |
| BaSnO$_{3-\delta}$ + SiO$_2$ 5 mol %*[4] 1400° C. baking + Pt 100 ppm | 1.0 | 1.02 | 0.22 |
| SnO$_2$ + SiO$_2$ 5 mol % 1400° C. baking | up to 10 | up to 3 | 0.20 |
| SnO$_2$ + SiO$_2$ 5 mol % 1400° C. baking + Pt 100 ppm | up to 10 | up to 3 | 0.20 |

*[1]At 900° C. for 4 hours, the specimens are subjected to repeated cycles of 4-second periods including 3 seconds in an atmosphere if $\lambda = 0.8$ and 1 second in an atmosphere of $\lambda = 1.05$ at 700° C. and checked for the resulting variation in resistance value to determine the ratio of the initial resistance value to the value after the endurance test,
*[2]the ratio of the resistance value at 1,000 ppm of CO to that at 10,000 ppm of CO, as determined at 700° C. in a system containing 4.6% of oxygen and N$_2$ in balance,
*[3]the variation in the resistance value due to the change in O$_2$ concentration from 1% to 10%, as evaluated using Rs = K · P · O$_2^m$,
*[4]the amount added of 1 $\mu$g per gram of the semiconductor is expressed as 1 ppm.

Pt-ZrO$_2$ Electrodes

Pt-ZrO$_2$ electrodes (10) and (12) are ZrO$_2$ deposited Pt in its crystal grain boundaries. These electrodes are manufactured, for example, by mixing Pt powders with ZrO$_2$ powders and subjecting the mixture to hot forging in the way of powder metallurgy. The added ZrO$_2$ is segregated in the crystal grain boundaries and is hardly contained inside the Pt crystal as a solid solution. The formation of solid solution, and the diffusion of such elements as Sn, etc., into the electrode are presumed to proceed through the crystal boundaries of Pt. The formation of the solid solution of such elements as Sn, etc., is intercepted by depositing $ZrO_2$ in the grain boundaries.

With regard to the amount of $ZrO_2$ added, 0.01~3.0% by weight is preferable; by using more than 0.01% by weight, sufficient corrosion resistance is achieved and by restraining it under 3.0% by weight, the hardness is restricted within a range conductive to easy machining. In this embodiment, the amount of $ZrO_2$ added was 0.6% by weight, but equivalent results were obtained with 0.3% by weight or 1.0% by weight. Accordingly, a more preferable amount of addition should be 0.1~2% by weight. While in the embodiment, the electrode's wire diameter is set at 70 $\mu$, arbitrary wire diameters may be chosen within a range where the electrode's proper mechanical strength may be assured, e.g., 50~300 $\mu$, or more preferably, 50~200 $\mu$. Further, Pt-Rh-$ZrO_2$ electrodes or Pt-Au-$ZrO_2$ electrodes etc., may be acceptable, if their main components are Pt.

Corrosion Resistance of Electrodes

For evaluation of electrodes for durability, the following tests are conducted with 6 each of gas sensors (2) of respective materials. Each sensor (2) is subjected to 20,000 cycles, one cycle being constituted by exposure to an atmosphere of 0.9$\lambda$ at 900° C. and to air at 350° each for 90 sec, to a total of 3 min. The total time for the cycles amounts to 1,000 hr. Midway in the course of these cycles, the sensor (2) is examined for any wire disconnection by measurement of its resistance value and upon ending the cycles the electrodes are checked. The 0.9$\lambda$ atmosphere is of a very strongly reducing nature as an atmosphere in which the gas sensors are placed and 900° C. corresponds to a maximum working temperature of gas sensors. Further, the temperature cycles at 350° C. and 900° C. impose a large thermal impact on the sensors. Accordingly, all these tests are rigorous in the aspects of atmosphere, maximum temperature and thermal impact.

Figure 3:
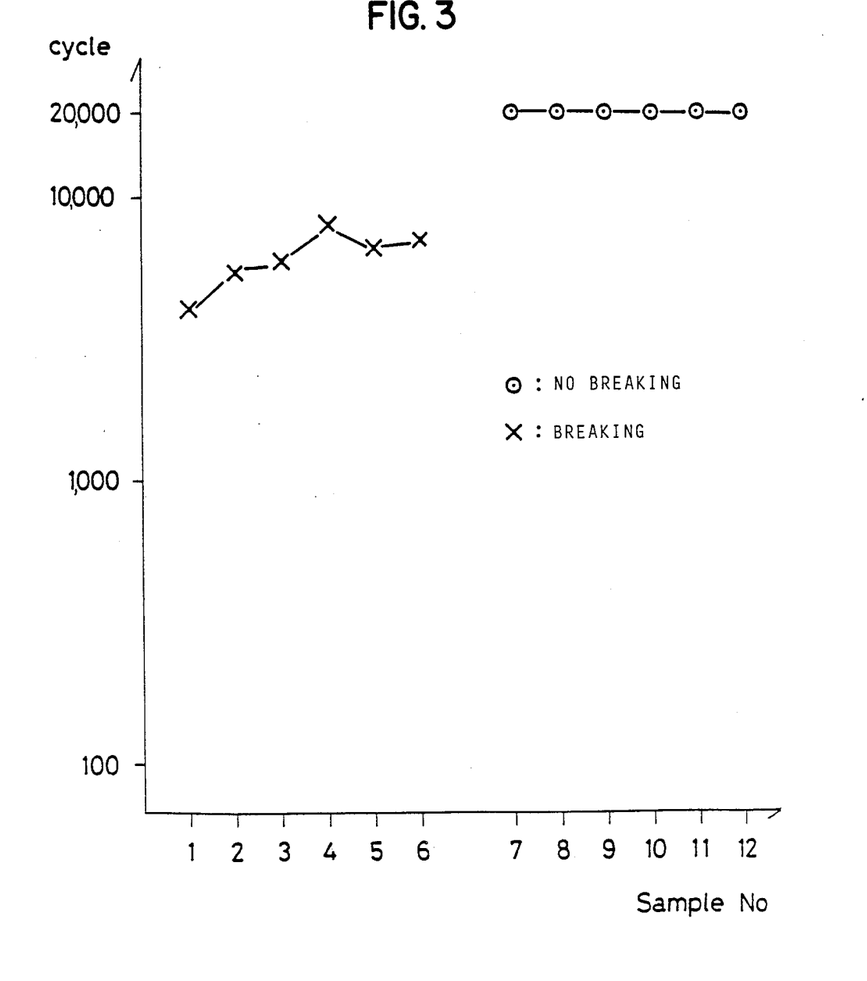
FIG. 3 is a characteristic graph showing corrosion resistance of the electrodes with respect to $BaSnO_3$.
Figure 4:
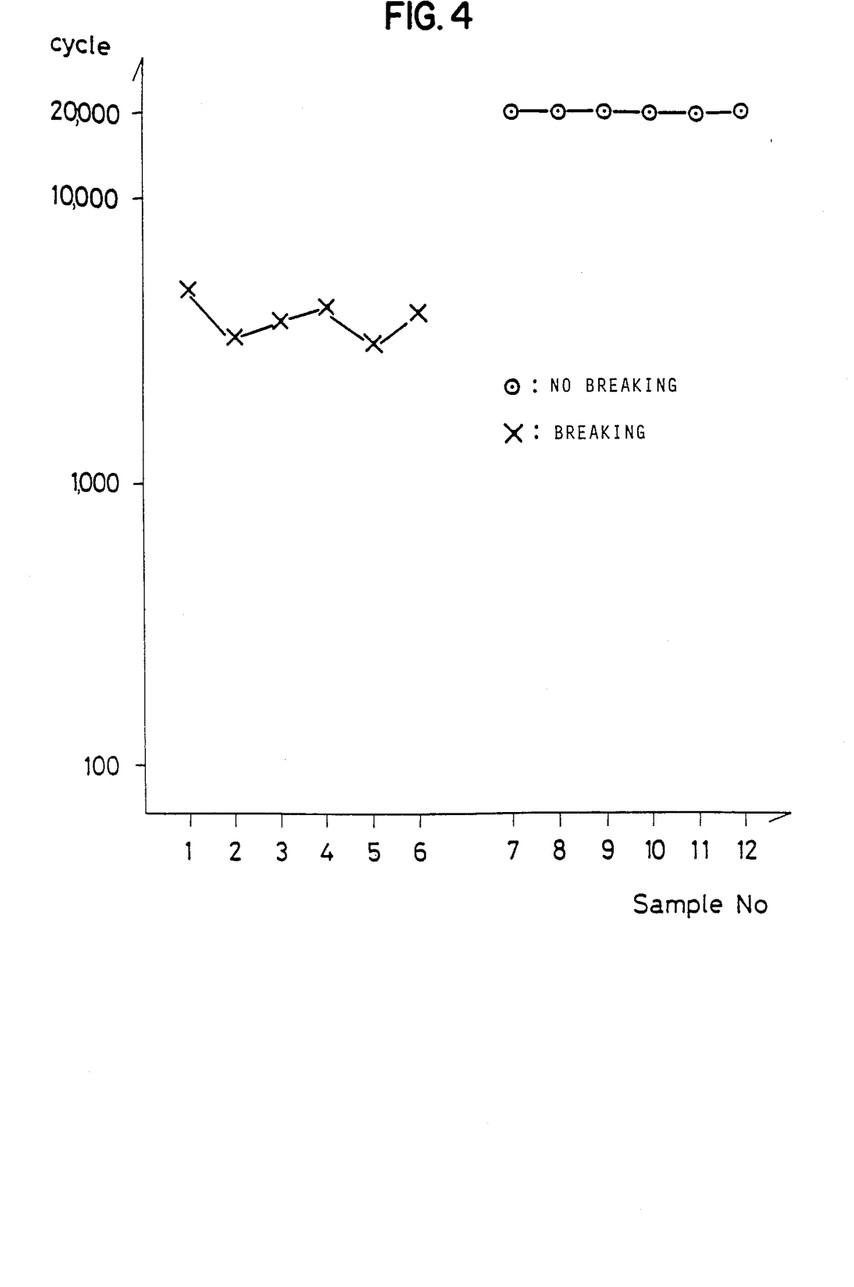
FIG. 4 is a characteristic graph showing corrosion resistance of the electrodes with respect to $SnO_2$.

FIG. 3 shows results obtained with $BaSnO_3$. In the case of samples 1~6 in which a Pt-Rh alloy (Rh 40% weight) of 80$\mu$ wire diameter was used, even though containing large amount of Rh and having a large wire diameter, all sustained breaking of wires. On the other hand, a Pt-$ZrO_2$ alloy of Samples 7~12 having a 70$\mu$ wire diameter and containing 0.6% by weight of $ZrO_2$, notwithstanding its diameter being small, did not sustain wire disconnection. It turned out from examination of the broken Pt-Rh alloy that Sn had diffused into the electrode interior to be alloyed therewith. On the other hand, in the Pt-$ZrO_2$ electrodes, Sn was existing merely in the surface part of the electrode as a solid solution of a low concentration, its diffusion being balked by $ZrO_2$ in the grain boundaries. FIG. 4 shows results of the same test conducted with $SnO_2$. Samples 1~6 are prepared by using the aforementioned Pt-Rh alloy, while samples 7~12 are formed with Pt-$ZrO_2$. The improvement in durability of electrodes by the use of Pt-$ZrO_2$ is commonly evident.

Test results with Sn base semiconductors are shown in Table 2:

TABLE 2

Durability of Electrodes (Sn base)

| No. | Semiconductor and additive to electrode (wt %)[1] | | Number of wires disconnected | Cycles taken before wire[2] breaking |
|---|---|---|---|---|
| 1* | $BaSnO_3$ | Rh40% | 6/6 | 6,000 |
| 2* | $BaSnO_3$ | Rh13% | 6/6 | — |
| 3 | $BaSnO_3$ | $ZrO_2$ 0.6% | 0 | — |
| 4* | $SnO_2$ | Rh40% | 6/6 | 4,000 |
| 5 | $SnO_2$ | $ZrO_2$ 0.6% | 0 | — |
| 6 | $SrSnO_3$ | $ZrO_2$ 0.6% | 0 | — |
| 7* | $CaSnO_3$ | Au5% | 5/6 | 8,000 |
| 8 | $CaSnO_3$ | $ZrO_2$ 0.6% | 0 | — |
| 9* | $SnO_2$ | Pt—$TiO_2$ | 4/6 | 13,000 |
| 10* | $TiO_2$ | Rh40% | 0 | — |
| 11 | $BaSnO_3$ | $ZrO_2$ 0.3% | 0 | — |
| 12 | $BaSnO_3$ | $ZrO_2$ 1.0% | 0 | — |

[1]In all samples, the main component of the electrode is Pt and the amount of the additive is given in % by weight concentration unit, Pt—$TiO_2$ indicates an electrode having $TiO_2$ added at 1.0% by weight concentration, the diameter of the electrode wire of Pt $ZrO_2$ and Pt—Au is 70$\mu$ while that of others 80$\mu$;
[2]Average value of cycle numbers counted before wire disconnection occurred to broken wires; and
*identifies comparative examples.

Figure 5:
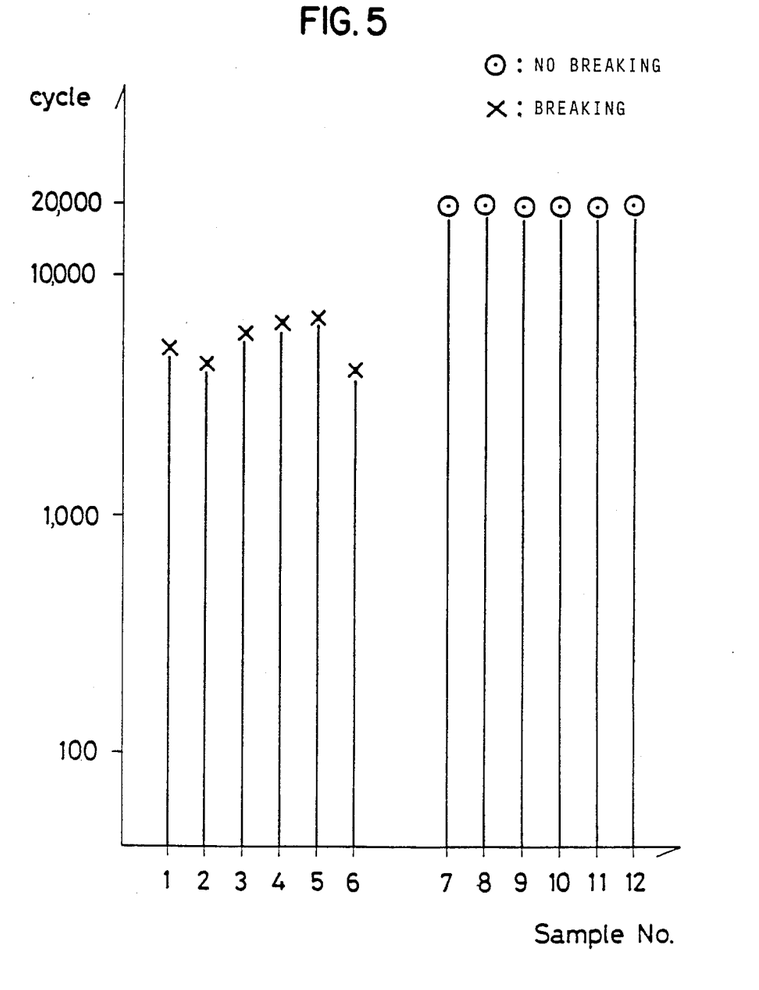
FIG. 5 is a characteristic graph showing corrosion resistance of the electrodes with respect to $SrFeO_3$.
Figure 6:
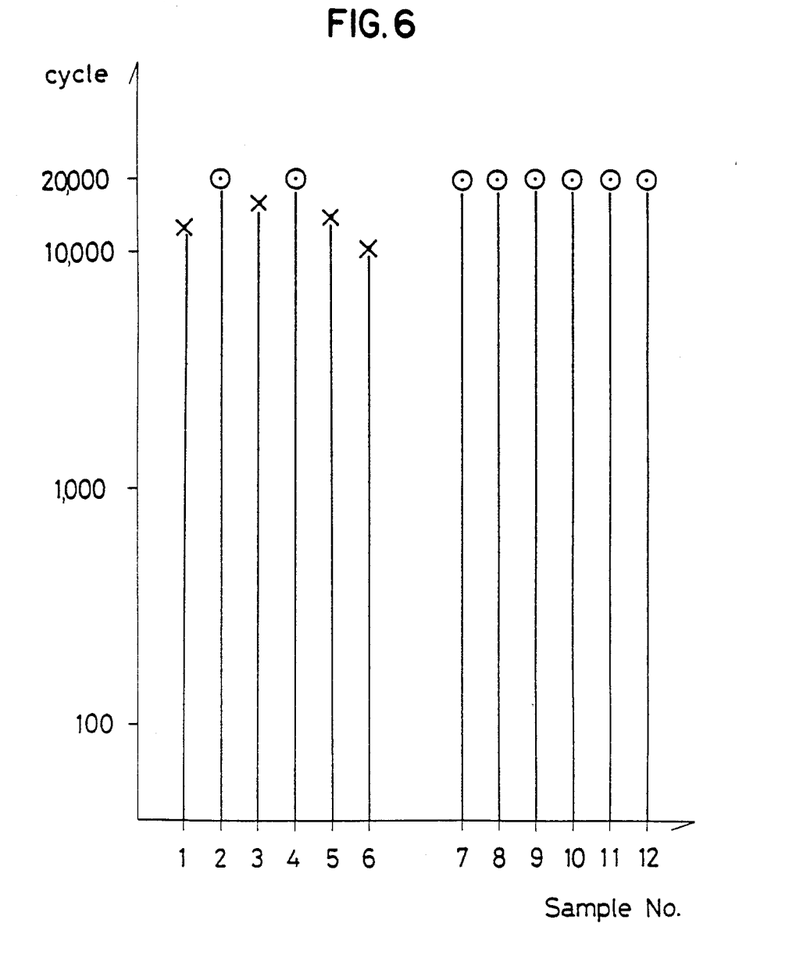
FIG. 6 is a characteristic graph showing the corrosion resistance of the electrodes with respect to $LaNiO_3$.
Figure 7:
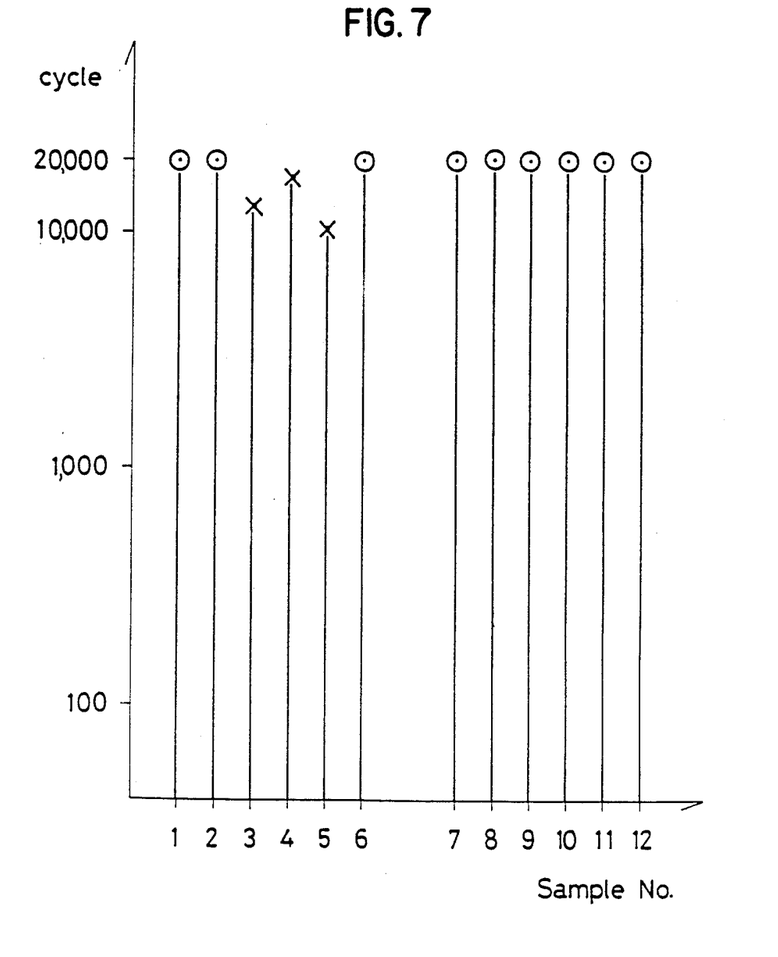
FIG. 7 is a characteristic graph showing the corrosion resistance of the electrodes with respect to $LaCoO_3$.

FIG. 5 gives results with $SrFeO_3$, FIG. 6 those with $LaNiO_3$, and FIG. 7 those with $LaCoO_3$. The measuring method used is similar to the case of $BaSnO_3$ and the enhancements in durability are similarly achieved with use of the Pt-$ZrO_2$ electrodes. And the corrosions similarly result from alloy formation from Pt with Fe, etc. These results are exhibited in Table 3, together with results to $SrFeO_3$ with Pt-$TiO_2$ electrodes.

TABLE 3

Durability of Electrodes (Fe, Ni and Co)

| No. | Semiconductor and additive to electrode (wt %)[1] | | Number of wires disconnected | Cycles taken before wire[2] breaking |
|---|---|---|---|---|
| 1* | $SrFeO_3$ | Rh40% | 6/6 | 5,000 |
| 2 | $SrFeO_3$ | $ZrO_2$ | 0 | — |
| 3* | $LaNiO_3$ | Rh40% | 4/6 | 13,000 |
| 4 | $LaNiO_3$ | $ZrO_2$ | 0 | — |
| 5* | $LaCoO_3$ | Rh40% | 3/6 | 13,000 |
| 6 | $LaCoO_3$ | $ZrO_2$ | 0 | — |
| 7* | $SrFeO_3$ | Pt-$TiO_2$ | 4/6 | 16,000 |

[1]In all samples, the main component of the electrode is Pt and the amount of the additive is given in % by weight concentration unit, in addition, "$ZrO_2$" indicates an electrode having $ZrO_2$ added at 0.6 wt % concentration, while Pt—$TiO_2$ indicates an electrode having $TiO_2$ added at 1.0 wt % concentration, the diameter of the electrode wire of Pt—$ZrO_2$ is 70$\mu$, while that of others 80$\mu$;
[2]Average value of cycle numbers counted before wire disconnection occurred to broken wires; and
*identifies comparative examples.

In these embodiments, results with specified semiconductors are shown. The enhancement of durability by the use of Pt-$ZrO_2$ electrodes is similarly achieved, when the type of semiconductors and their conditions of preparation are altered. Corrosions result from alloying Pt with respective elements in the semiconductors - Sn, Fe, Ni and Co, so, even if $LaCoO_3$ is substituted by $NdCoO_3$, for example, the cause and mechanism of corrosion still remain unchanged. They are not changed by the choice of the starting material of the semiconductor or its baking conditions, either.

What is claimed is:

1. An exhaust gas sensor of the type comprising a metal oxide semiconductor which undergoes change in resistance value due to presence of gases, and at least one pair of electrodes connected with the metal oxide semiconductor, the improvement comprising the metal oxide semiconductor, containing at least one member of a group of elements consisting of Sn, Fe, Ni and Co, the main component of said electrodes being Pt or a platinum alloy, with $ZrO_2$ being deposited only in crystalline grain boundaries of the electrodes.

2. An exhaust gas sensor as claimed in claim 1, wherein the metal oxide semiconductor is a perovskite compound $ASnO_3$ where A represents at least one member of a group of elements consisting of Ca, Sr and Ba.

3. An exhaust gas sensor as claimed in claim 2, wherein the perovskite compound $ASnO_3$ is $BaSnO_3$.

4. An exhaust gas sensor as claimed in claim 1, wherein the metal oxide semiconductor is a perovskite compound $LnBO_3$ where Ln represents at least one member of a group of elements consisting of lanthanides elements with atomic numbers 57 to 71 and alkaline earth elements, and B represents at least one member of a group of elements consisting of Fe, Ni and Co.

5. An exhaust gas sensor as claimed in claim 4, wherein the perovskite compound $LnBo_3$ denotes at least one member of a group of compounds consisting of $SrFeO_3$, $LaNiO_3$ and $LaCoO_3$.

6. An exhaust gas sensor as claimed in claim 1, wherein the $ZrO_2$ content in the electrodes is 0.01 to 3% by weight.

7. An exhaust gas sensor as claimed in claim 6, wherein the $ZrO_2$ content in the electrodes is 0.1 to 2% by weight.

8. The exhaust gas sensor of claim 1 wherein the main component of said electrodes is Pt.

9. The exhaust gas sensor of claim 1 wherein the main component of said electrodes is a Pt alloy such as Pt-Rh or Pt-Au.

* * * * *